(12) United States Patent
Hightower et al.

(10) Patent No.: US 12,115,205 B2
(45) Date of Patent: *Oct. 15, 2024

(54) ALVOECORE A RESPIRATORY SYSTEM PROTECTION PRODUCT AND IMMUNE SYSTEM BOOSTER

(71) Applicants: Herbert Hightower, Temple, TX (US); Bachmai N-Hightower, Temple, TX (US); Milton S. Arline, Iron City, GA (US); Jordan Reid, Miami Garden, FL (US); Jordan Arline, Donaldsonville, GA (US)

(72) Inventors: Herbert Hightower, Temple, TX (US); Bachmai N-Hightower, Temple, TX (US); Milton S. Arline, Iron City, GA (US); Jordan Reid, Miami Garden, FL (US); Jordan Arline, Donaldsonville, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/246,163

(22) PCT Filed: Sep. 26, 2022

(86) PCT No.: PCT/US2022/044727
§ 371 (c)(1),
(2) Date: Mar. 21, 2023

(87) PCT Pub. No.: WO2023/140900
PCT Pub. Date: Jul. 27, 2023

(65) Prior Publication Data
US 2023/0285494 A1    Sep. 14, 2023

Related U.S. Application Data

(62) Division of application No. 17/935,418, filed on Sep. 26, 2022, now abandoned.

(60) Provisional application No. 63/300,839, filed on Jan. 19, 2022.

(51) Int. Cl.
| | | |
|---|---|---|
| *A61K 36/886* | (2006.01) | |
| *A61K 9/08* | (2006.01) | |
| *A61K 36/00* | (2006.01) | |
| *A61K 36/185* | (2006.01) | |
| *A61K 36/53* | (2006.01) | |
| *A61K 36/61* | (2006.01) | |
| *A61K 47/02* | (2006.01) | |
| *A61K 47/08* | (2006.01) | |
| *A61K 47/46* | (2006.01) | |

(52) U.S. Cl.
CPC .............. *A61K 36/886* (2013.01); *A61K 9/08* (2013.01); *A61K 36/185* (2013.01); *A61K 36/53* (2013.01); *A61K 36/61* (2013.01); *A61K 47/02* (2013.01); *A61K 47/08* (2013.01); *A61K 47/46* (2013.01); *A61K 2236/13* (2013.01); *A61K 2236/31* (2013.01); *A61K 2236/331* (2013.01); *A61K 2236/37* (2013.01)

(58) Field of Classification Search
None
See application file for complete search history.

(56) References Cited

U.S. PATENT DOCUMENTS

| | | |
|---|---|---|
| 4,735,935 A | 4/1988 | McAnalley |
| 5,587,364 A | 12/1996 | McAnalley et al. |
| 5,786,342 A | 7/1998 | Carpenter et al. |
| 9,561,271 B2 | 2/2017 | Fattom et al. |
| 10,561,698 B2 | 2/2020 | Mouser |
| 10,849,952 B2 | 12/2020 | Mouser |
| 2008/0219938 A1 | 9/2008 | Grune |
| 2015/0110905 A1 | 4/2015 | Darsale |
| 2020/0197475 A1 | 6/2020 | Duncan et al. |
| 2020/0281998 A1 | 9/2020 | Scharp et al. |
| 2023/0226134 A1* | 7/2023 | Hightower ............. A61K 47/46 424/744 |
| 2023/0285494 A1* | 9/2023 | Hightower ............. A61K 47/02 424/744 |

FOREIGN PATENT DOCUMENTS

CN    108926500 A    4/2018

OTHER PUBLICATIONS

Aburita Gupta, Health Benefits: Why Aloe Vera is Great for You, Healthy Living, Jul. 4, 2023, The Metrognome, retrieved from internet, retrieved on Sep. 26, 2022, <URL: https://www.indiatimes.com/health/healthyliving/health-benefits-why-aloe-vera-is-great-for-you-242977.html>.

Jeong-Hwan Hwang, et al., Effect of processed aloe vera gel on immunogenicity in inactivated quadrivalent influenza vaccine and upper respiratory tract infection in healthy adults: A randomized double-blind placebo-controlled trial, Phytomedicine, Oct. 2021, vol. 91, Elsevier GmbH, retrieved from internet, retrieved on Sep. 26, 2022, <URL: https://doi.org/10.1016/j.phymed.2021.153668>.

Petra Bastin, et al., Candelabra aloe (*Aloe arborescens*) in the therapy and prophylaxis of upper respiratory tract infections: traditional use and recent research results, Wien Med Wochenschr, Jan. 30, 2013, vol. 163, pp. 73-79, retrieved from internet, retrieved on Sep. 26, 2022, <URL: https://pubmed.ncbi.nlm.nih.gov/23361849/>.

* cited by examiner

*Primary Examiner* — Aaron J Kosar
*Assistant Examiner* — Randall O Winston

(57) ABSTRACT

The present invention is a respiratory system protection product and a method for creating said product. The product is created by separating an aloe vera gel from a quantity of aloe vera leaves. The aloe vera gel is added to a heating vessel. A first solution is prepared and added to cover the aloe vera gel. The heating vessel is covered, heated, and stirred until boiling, then removed from heat. After cooling to room temperature an oil component is added. The mixture is blended and amalgamated, then filtered to remove solid materials.

12 Claims, 1 Drawing Sheet

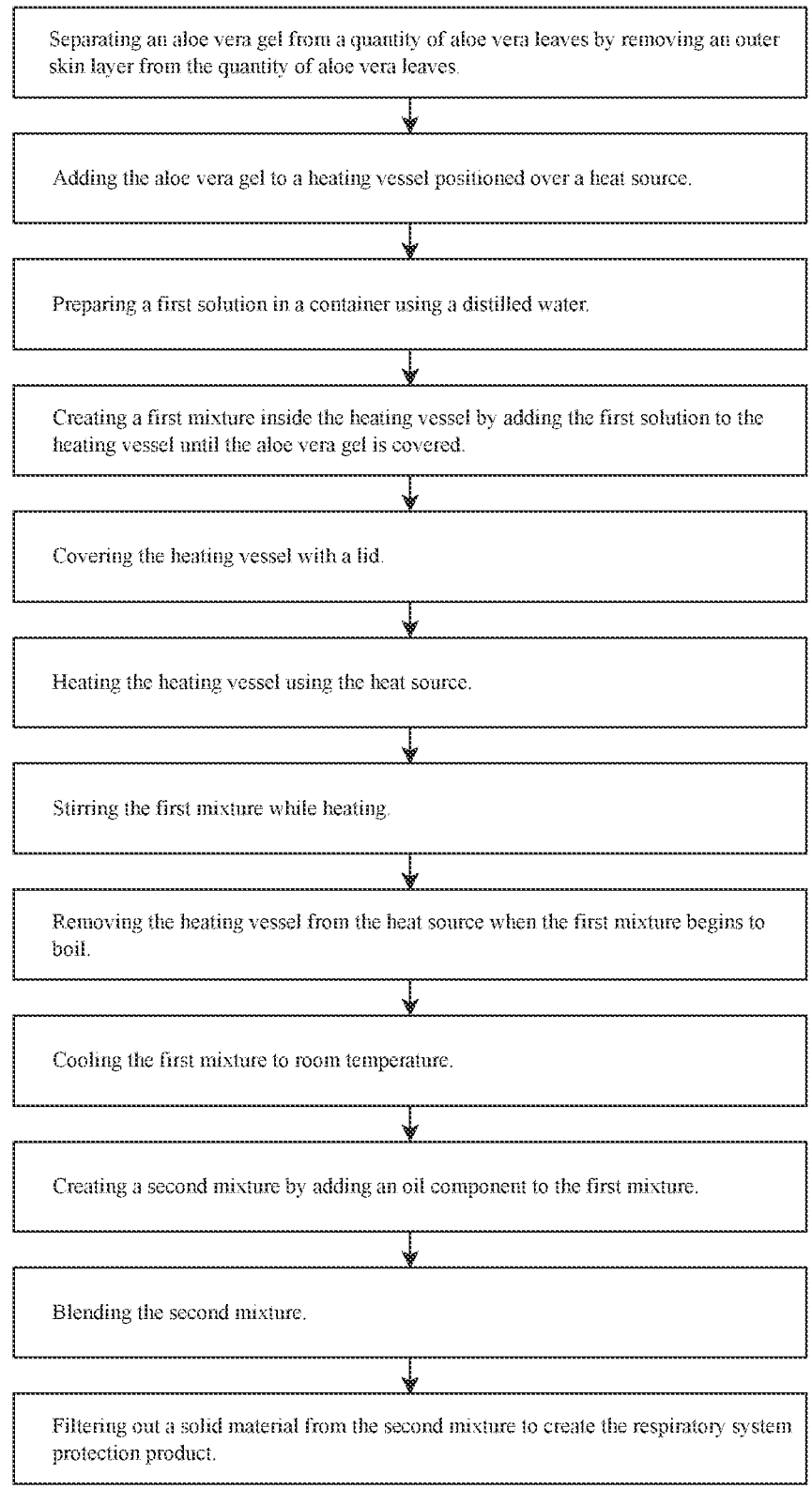

ALVOECORE A RESPIRATORY SYSTEM PROTECTION PRODUCT AND IMMUNE SYSTEM BOOSTER

FIELD OF THE INVENTION

The present invention relates generally to a respiratory therapy. More specifically, the present disclosure describes a method for creating a product designed as a Respiratory System Protective Product that also greatly enhances and boosts one's immune system.

BACKGROUND OF THE INVENTION

In order to maintain good overall health, a strong and healthy respiratory system is required. The respiratory system continually breathes in and absorbs oxygen while breathing out carbon dioxide. Further, the respiratory system is responsible for filtering out and removing debris, droplets, and other matter that are constantly circulated through its system. Any illness or infection that affects the respiratory system has detrimental to a person's overall health.

While deep breathing exercises and good hygiene help maintain a healthy respiratory system, there is still a need for a product that helps improve breathing, boosts the immune system, and aids the respiratory system in cleaning and protecting itself.

SUMMARY OF THE INVENTION

The present invention, Alvoecore, provides a level of respiratory system protection that is unmatched by anything on the market today. Alvoecore is safe, effective, and works in less than 24 hours.

Further the present invention keeps the complex linings of the nose hydrated, improving their ability to act as a trap for inhaled particles. At the same time the present invention helps to support healthy cilia activity which aids in moving mucus and trapped particles out of the sinus and nasal cavities, leading to clear and comfortable sinus and nasal passages.

Alvoecore further treats and prevents many common respiratory illnesses such as colds, flus, viruses, and COVID-19, while improving the user's immune system.

Alvoecore is easily administered using one of several means including: topical, spray-on, roll-on, wipes, and can also be applied to facemasks.

An objective of the present invention is to provide a product that prevents, treats, and cures respiratory illnesses such as: colds, flu, sinus infections, sinus congestion, COVID-19 virus, and other types of respiratory illnesses.

A further objective of the present invention is to fight respiratory infection and inflammation of the bronchial tubes such as bronchitis.

An even further objective of the present invention is to enhance and boost the user's immune system, mood, and energy levels.

Another objective of the present invention is to aid in expelling coughs, easing sore throats, reducing fevers, and draining sinuses.

Yet a further objective of the present invention is to provide a product that is easy to administer.

A further objective of the present invention is to manage allergies, relieve headaches, and provide pain relief.

BRIEF DESCRIPTION OF THE DRAWINGS

FIG. 1 shows a flowchart of the preferred method of the present invention.

DETAIL DESCRIPTIONS OF THE INVENTION

All illustrations of the drawings are for the purpose of describing selected versions of the present invention and are not intended to limit the scope of the present invention.

The present invention is a product having been designed as a "Respiratory System Protective Product" that also greatly enhance and boost one's immune system.

Some of the ingredients that are used during the creation of the present invention include: aloe vera, lavender essential oil, eucalyptus essential oil, distilled water, distilled witch hazel, hydrogen peroxide, distilled white vinegar, and distilled alcohol.

Aloe vera (or Aloe) is a cactus-like plant that grows in hot, dry climates. The aloe vera leaves have an outer skin layer that is green and thick. The inside of the aloe vera leaves contains a clear white aloe vera gel material. The aloe vera gel has been traditionally used to treat and soothe burns and abrasions of the skin. Further uses for aloe vera include ingesting the gel to promote weight loss and treat inflammatory bowel disease. Even further uses and benefits include managing allergies, expelling coughs, draining sinuses, relieving headaches, easing sore throats, boosting immunity, and improving mood and energy levels.

Lavender essential oil is created by steaming or pressing portions of the lavender plant. This process extracts an oil with the fragrance and medicinal qualities of the lavender plant.

Lavender plants have traditionally been used as an aromatherapy and inhalation therapy to treat headaches, treat depression, reduce stress, treat sinus infections, relax the airways, and improve breathing. Further, lavender has antiseptic and anti-inflammatory properties which allow it to be used for treating and curing infections and reducing inflammation.

Eucalyptus essential oil is created by steaming or pressing the leaves of the eucalyptus plant. This process extracts an oil with the fragrance and medicinal qualities of the eucalyptus plant.

Eucalyptus has a history of being used to treat many respiratory issues such as sinus infections, nasal congestion, coughing, asthma, and improving breathing. Further, eucalyptus has been used topically to treat arthritis and skin ulcers. Eucalyptus has even further use as an aromatherapy treatment.

The present invention is created using distilled water. Distilled water is used because the use of an unpurified water, such as tap water would lead to the introduction of chemicals such as chlorine or fluorine. Further, hard water should also be avoided.

Distilled witch hazel is extracted and distilled leaves, barks, and twigs of the witch hazel plant. Distilled witch hazel is a natural remedy that has traditionally been used for treating skin related issues, the relief of itching, and to reduce swelling and inflammation. Further, it can be ingested to treat coughs and fevers.

Hydrogen peroxide has a chemical formula similar to water expect with an extra oxygen molecule. Hydrogen peroxide works by releasing the extra oxygen molecule, which creates a foam that helps to remove mucus and debris. Further, hydrogen peroxide has antiseptic properties that helps prevent infections.

Hydrogen peroxide is typically used as topical skin treatment for burns and abrasions, helping to remove debris and prevent infection. Hydrogen peroxide has been further used as a mouth rinse to remove mucus and treat infections or sores.

Distilled white vinegar is created by the fermentation and distillation of ethanol alcohol. Distilled white vinegar has a plurality of uses including cooking, cleaning, and as a medicine. As a medicine distilled white vinegar has been used to control blood sugar, reduce cholesterol, an antimicrobial, and an antifungal. Due to its antimicrobial and antifungal properties, distilled white vinegar has been used to treat nail fungus, warts, and ear infections.

Distilled alcohol is created through the fermentation and distillation of various precursors. Distilled alcohol has long been used as an antiseptic and disinfectant. Due to these strong antibacterial and disinfecting properties distilled alcohol is found in hand sanitizers, disinfecting sprays, and first aid disinfecting wipes.

The present invention is further compromised of a preferred method for creating a respiratory system protection product. The preferred method comprises separating an aloe vera gel from a quantity of aloe vera leaves by removing an outer skin layer from the quantity of aloe vera leaves.

The aloe vera leaves have a flattened triangular spiny shape. The exterior of the aloe vera leaves are covered in an outer skin layer. The outer skin layer is a green layer that is tough in nature and requires a knife or other sharp means to cut. The interior of the aloe vera leaves contains an aloe vera gel. The aloe vera gel being a white clear gel that is soft in nature and can be separated and removed from the outer skin layer by a spoon or other scraping means.

Once the aloe vera gel has been separated from the aloe vera leaves, the aloe vera gel should be cut into smaller chunks. The process of cutting the aloe vera gel into chunks helps it dissolve later during the process.

An alternate exemplary method of separating the aloe vera gel from the aloe vera leavers would be cutting the aloe vera leaves first into chunks using a knife and a cutting board. Then separating the aloe vera gel from the chunks.

The preferred method of the present invention further comprises adding the aloe vera gel to a heating vessel positioned over a heat source.

The heat source being turned off and the heating vessel being at room temperature, the heating vessel is place on top of the heat source. The heat source may comprise of a number of different heating means such as but not limited to a stove, a propane burner, or an electric hotplate.

The heating vessel may comprise of a number of different means for containing and heating a liquid mixture such as but not limited to a pot, or a kettle. The aloe vera gel is added into the heating vessel.

The preferred method further comprises preparing a first solution in a container using distilled water. The first solution being comprised of distilled water and for each 1 gallon of the distilled water the first solution further comprises: 1 tablespoon distilled witch hazel, 1 tablespoon hydrogen peroxide, 1 tablespoon distilled alcohol, and 1 tablespoon white vinegar.

The container used to prepare the first solution can be any container which is capable of holding liquid such as but not limited to a pitcher, a flask, or a bottle.

Now with the first solution prepared, a first mixture is created inside the heating vessel by adding the first solution to the heating vessel until the aloe vera gel is covered, so that none of the aloe vera gel is above the surface level of the first mixture.

The heating vessel used in the preferred method should have the capacity to hold or contain a volume greater than double the volume of the first mixture.

The heating vessel is covered with a lid. The lid being any suitable means for covering the top of the heating vessel while heating such as a pot lid. The heat source is turned on and the heating vessel along with the first mixture is heated.

In an alternative exemplary embodiment the heating source is comprised of a stove and the heating vessel is comprised of a pot. The stove is turned on to high or full heat for 3 minutes. The stove is then reduced down to half or medium heat.

In the preferred embodiment of the present invention, the first mixture is stirred during the heating process. Stirring can be completed by a number of means for stirring such as but not limited to using a spatula or a spoon.

When the first mixture begins to boil, the heating vessel is removed from the heat source. This is done to stop the heating process and prevent the first mixture from overheating. Once the heating vessel is removed from the heat source, the first mixture begins to cool.

The first mixture is allowed to cool until it reaches room temperature. Room temperature being the ambient temperature of the room, typical values would range between 70-80 degrees Fahrenheit. After the first mixture reaches room temperature a second mixture is created by adding an oil component to the first mixture.

In the preferred embodiment for each 1 gallon of the first mixture the oil component comprises: 12.5 milliliters eucalyptus essential oil, and 12.5 milliliters lavender essential oil.

If the oil component is added while the first mixture is still hot, the oil component would lose some of their medicinal value. Therefore, it is important that the first mixture cools to room temperature before the addition of the oil component.

The second mixture is blended to ensure all of the ingredients are blended or amalgamated together. The blending process also helps to break down any remaining chunks or large pieces. The blending can be accomplished through any means of blending such as but not limited to using a blender.

The second mixture is filtered to remove any solid material from the second mixture. The solid material being any non liquid materials. The second mixture is filtered using any suitable means for filtering such as but not limited to pouring through a mesh strainer, a mesh screen, or a filtering media. The solid material may be discarded.

The respiratory system protection product is comprised of the remaining liquid from the second mixture after filtering. The respiratory system protection product maybe stored at room temperature.

The present invention further comprises a respiratory system protection product that is produced by the methods of the present invention. This respiratory system protection product can be used as a topical agent that is applied to the chest, neck, and head areas. Further this respiratory system protection product can be administered through several means including but not limited to topical, spray-on, wipes, or roller applications. Further the present invention maybe applied alongside or to the inside of facemasks.

After application, the present invention provides a plurality of benefits to the users such as but not limited to treating and curing colds, flus, sinus infections, and sinus congestion. Further the present invention boosts the immune system and aids in respiratory function.

Although the invention has been explained in relation to its preferred embodiment, it is to be understood that many other possible modifications and variations can be made without departing from the spirit and scope of the invention.

What is claimed is:

1. A method for creating a respiratory system protection product comprising:
    separating an aloe vera gel from a quantity of aloe vera leaves by removing an outer skin layer from the quantity of aloe vera leaves;
    adding the aloe vera gel to a heating vessel positioned over a heat source;
    preparing a first solution in a container using a distilled water;
    creating a first mixture inside the heating vessel by adding the first solution to the heating vessel until the aloe vera gel is covered;
    covering the heating vessel with a lid;
    heating the heating vessel using the heat source;
    stirring the first mixture while heating;
    removing the heating vessel from the heat source when the first mixture begins to boil;
    cooling the first mixture to room temperature;
    creating a second mixture by adding an oil component to the first mixture;
    blending the second mixture; and
    filtering out a solid material from the second mixture to create the respiratory system protection product.

2. The method of claim 1, wherein for each 1 gallon of the distilled water the first solution comprises:
    1 tablespoon distilled witch hazel;
    1 tablespoon hydrogen peroxide;
    1 tablespoon distilled alcohol; and
    1 tablespoon white vinegar.

3. The method of claim 1, wherein the heating vessel comprises a cooking pot capable of containing a volume which is greater than double the first mixture.

4. The method of claim 3, wherein the heat source comprises a stove.

5. The method of claim 1, wherein for each 1 gallon of the first mixture the oil component comprises:
    12.5 milliliters eucalyptus essential oil; and
    12.5 milliliters lavender essential oil.

6. The method of claim 1, wherein blending the second mixture comprises a blender.

7. The method of claim 1, wherein filtering out the solid material comprising pouring the second mixture through a mesh strainer.

8. A method for creating a respiratory system protection product comprising:
    separating an aloe vera gel from a quantity of aloe vera leaves by removing an outer skin layer from the quantity of aloe vera leaves;
    adding the aloe vera gel to a heating vessel positioned over a heat source;
    preparing a first solution in a container using a distilled water;
    wherein for each 1 gallon of the distilled water the first solution comprises:
    1 tablespoon distilled witch hazel;
    1 tablespoon hydrogen peroxide;
    1 tablespoon distilled alcohol;
    1 tablespoon white vinegar,
    creating a first mixture inside the heating vessel by adding the first solution to the heating vessel until the aloe vera gel is covered;
    covering the heating vessel with a lid;
    heating the heating vessel using the heat source;
    stirring the first mixture while heating;
    removing the heating vessel from the heat source when the first mixture begins to boil;
    cooling the first mixture to room temperature;
    creating a second mixture by adding an oil component to the first mixture;
    wherein for each 1 gallon of the first mixture the oil component comprises:
    12.5 milliliters eucalyptus essential oil;
    12.5 milliliters lavender essential oil;
    blending the second mixture; and
    filtering out a solid material from the second mixture to create the respiratory system protection product.

9. The method of claim 8, wherein the heating vessel comprises a cooking pot capable of containing a volume which is greater than double the first mixture.

10. The method of claim 9, wherein the heat source comprises a stove.

11. The method of claim 8, wherein blending the second mixture comprises a blender.

12. The method of claim 8, wherein filtering out the solid material comprising pouring the second mixture through a mesh strainer.

* * * * *